US009371554B2

United States Patent
McNerney et al.

(10) Patent No.: US 9,371,554 B2
(45) Date of Patent: Jun. 21, 2016

(54) FLOCCULATION METHOD

(71) Applicant: Amgen Inc., Thousand Oaks, CA (US)

(72) Inventors: Thomas M McNerney, Sammamish, WA (US); Krista Petty, Newbury Park, CA (US); Anne C Thomas, Kenmore, WA (US); Xiaoyang Zhao, Moorpark, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/365,496

(22) PCT Filed: Dec. 14, 2012

(86) PCT No.: PCT/US2012/069916
§ 371 (c)(1),
(2) Date: Jun. 13, 2014

(87) PCT Pub. No.: WO2013/090820
PCT Pub. Date: Jun. 20, 2013

(65) Prior Publication Data
US 2015/0004646 A1    Jan. 1, 2015

Related U.S. Application Data

(60) Provisional application No. 61/576,303, filed on Dec. 15, 2011.

(51) Int. Cl.
*C12P 21/00* (2006.01)
*C12P 21/02* (2006.01)
*C07K 1/14* (2006.01)

(52) U.S. Cl.
CPC ................. *C12P 21/00* (2013.01); *C07K 1/145* (2013.01); *C12P 21/02* (2013.01)

(58) Field of Classification Search
None
See application file for complete search history.

(56) References Cited

U.S. PATENT DOCUMENTS 5,552,316 A    9/1996   Savage

FOREIGN PATENT DOCUMENTS

| CA | 2 380 652 A1 | 2/2001 |
| EP | 1403274 A1 | 3/2004 |
| WO | 01/12778 A2 | 2/2001 |
| WO | 2008/100578 A2 | 8/2008 |
| WO | 2010/082894 A1 | 7/2010 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Berrill, et al., "Ultra scale-down to define and improve the relationship between flocculation and disc-stack centrifugation," Biotech. Progress vol. 24, No. 2, pp. 426-431 (2008).
Riske, et al., "The use of chitosan as a flocculant in mammalian cell culture dramatically improves clarification throughput without adversely impacting monoclonal antibody recovery," J. Biotechnology vol. 128, No. 4, pp. 813-823 (2007).
Yukselen, et al., "Formulation and breakage of flocs using dual polymers," Water Science & Technology, vol. 53, No. 7, pp. 217-223 (2006).

* cited by examiner

*Primary Examiner* — Christian Fronda
(74) *Attorney, Agent, or Firm* — Randolph N. Mohr

(57) ABSTRACT

The present invention relates to a method for harvesting recombinant proteins from mammalian cell culture fluid. The method makes use of cationic polymers, non-ionic polymers and non-ionic surfactants.

19 Claims, 11 Drawing Sheets

FLOCCULATION METHOD

CROSS REFERENCE TO RELATED APPLICATIONS

This application is a national stage application under 35 U.S.C. §371 of International Application No. PCT/US2012/069916, having an international filing date of Dec. 14, 2012; which claims priority to U.S. Provisional Patent Application No. 61/576,303, filed Dec. 15, 2011, which is incorporated herein by reference.

FIELD OF INVENTION

The present invention relates to a method for harvesting recombinant proteins from mammalian cell culture broth. The method makes use of cationic polymers, non-ionic polymers and non-ionic surfactants.

BACKGROUND OF INVENTION

Clinical manufacture of therapeutic proteins is an expensive, large scale endeavor. Demand for greater quantities of therapeutic recombinant proteins has driven advances in cell culture processing which have resulted in dramatically increased product titer. High titer cell culture processes are typically produced by maintaining high viable cell densities over longer culture durations. A corresponding increase in the biomass solids (viable and non-viable cells) and the submicron cellular debris particles are also observed. The higher burden of solids and submicron cellular debris particles can challenge mammalian cell culture harvest processes, making the harvest process less effective at removing the debris without a substantial loss of product capacity.

Cationic polymer flocculents are used for many applications ranging from potable water purification, waste water treatment, uses in the petroleum, mining and paper making industries, cosmetics and medical uses, and have also been used to encapsulate mammalian cells and enzymes and to flocculate microbial cell cultures. However, for use in a commercial scale mammalian cell harvest process, lengthy flocculation settling time can be problematic, resulting in a harvest process that is time consuming and less efficient than standard harvest practices.

There is a continuing need to improve mammalian cell culture harvest methods, particularly commercial scale methods. Any improvements that allow for quicker recovery times and/or greater recovery can lead to reduced costs associated with manufacturing protein therapeutics. The invention fulfills this need by providing a quick and efficient method of cell culture harvest.

SUMMARY OF THE INVENTION

The present invention provides a mammalian cell culture harvest method comprising culturing mammalian cells expressing a recombinant protein in a cell culture medium for a predetermined time or until a desired cell density and/or packed cell volume is achieved, adding a cationic polymer and a non-ionic polymer to the cell culture medium initiating flocculation, mixing the cell culture medium during flocculation, allowing the flocculent to settle, and recovering the clarified supernatant.

The present invention also provides a mammalian cell culture harvest method comprising culturing mammalian cells expressing a recombinant protein in a cell culture medium for a predetermined time or until a desired cell density and/or packed cell volume is achieved, adding poly diallyldimethyammonium chloride and PEG 3,000 to the cell culture medium initiating flocculation, mixing the cell culture medium during flocculation, allowing the flocculent to settle, and recovering the clarified supernatant.

The present invention also provides a mammalian cell culture harvest method comprising culturing mammalian cells expressing a recombinant protein in a cell culture medium for a predetermined time or until a desired cell density and/or packed cell volume is achieved, adding poly diallyldimethyammonium chloride, PEG 3,000 and Triton X-100 to the cell culture medium initiating flocculation, mixing the cell culture medium during flocculation, allowing the flocculent to settle, and recovering the clarified supernatant.

The present invention also provides a mammalian cell culture harvest method comprising culturing mammalian cells expressing a recombinant protein in a cell culture medium for a predetermined time or until a desired cell density and/or packed cell volume is achieved, adding a cationic polymer and a non-ionic polymer to the cell culture medium initiating flocculation, mixing the cell culture medium during flocculation, allowing the flocculent to settle for a primary settle, recovering the primary clarified supernatant, washing the primary settle flocculent, allowing the washed flocculent to settle for a secondary settle, and recovering the secondary clarified supernatant.

The present invention also provides a mammalian cell culture harvest method comprising culturing mammalian cells expressing a recombinant protein in a cell culture medium for a predetermined time or until a desired cell density and/or packed cell volume is achieved, adding a cationic polymer and a non-ionic polymer to the cell culture medium initiating flocculation, mixing the cell culture medium during flocculation, allowing the flocculent to settle for a primary settle, recovering the primary clarified supernatant, washing the primary settle flocculent if product recovery in the primary clarified supernatant is less than 80%, allowing the washed flocculent to settle for a secondary settle, and recovering the secondary clarified supernatant.

The present invention also provides a mammalian cell culture harvest method comprising culturing mammalian cells expressing a recombinant protein in a cell culture medium for a predetermined time or until a desired cell density and/or packed cell volume is achieved, adding poly diallyldimethyammonium chloride and PEG 3,000 to the cell culture medium initiating flocculation, mixing the cell culture medium during flocculation, allowing the flocculent to settle for a primary settle, recovering the primary clarified supernatant, washing the primary settle flocculent, allowing the washed flocculent to settle for a secondary settle, and recovering the secondary clarified supernatant.

The present invention also provides a mammalian cell culture harvest method comprising culturing mammalian cells expressing a recombinant protein in a cell culture medium for a predetermined time or until a desired cell density and/or packed cell volume is achieved, adding poly diallyldimethyammonium chloride, PEG 3,000 and Triton X-100 to the cell culture medium initiating flocculation, mixing the cell culture medium during flocculation, allowing the flocculent to settle for a primary settle, recovering the primary clarified supernatant, washing the primary settle flocculent, allowing the washed flocculent to settle for a secondary settle, and recovering the secondary clarified supernatant.

In one embodiment the cationic polymer is poly diallyldimethyammonium chloride.

In another embodiment the non-ionic polymer is selected from poly ethylene glycol and dextran.

In another embodiment the non-ionic polymer is selected from PEG 3,000 and PEG 6,000.

In another embodiment, the mammalian cell culture harvest methods provided above further comprise adding a non-ionic surfactant to the cell culture medium. In a related embodiment the non-ionic surfactant is Triton X-100.

In another embodiment, the cationic polymer and the non-ionic polymer are added simultaneously.

In another embodiment, the cationic polymer, the non-ionic polymer and the non-ionic surfactant are added simultaneously.

In another embodiment, the cationic polymer is added first and mixed for at least 30 seconds followed by addition of the non-ionic polymer.

In another embodiment, the cationic polymer is added first and mixed for at least 30 seconds followed by addition of the non-ionic polymer and a non-ionic surfactant.

In another embodiment, the cationic polymer is a polymer of diallyldimethylammonium chloride, polydiallyldimethylammonium chloride, polyethyleneimine, polyacrylamide or chitosan.

In another embodiment, the non-ionic surfactant is Sapoin or Triton X100.

In another embodiment, the poly diallyldimethyammonium chloride is added at a concentration of at or about 20 to at or about 90 pg/total cell density.

In another embodiment the poly diallyldimethyammonium chloride is added at a concentration of at or about 25 pg/total cell density wherein the mammalian cells originate from a diploid cell line.

In another embodiment, the poly diallyldimethyammonium chloride is added between 43 pg/total cell density and 57 pg/total cell density wherein the mammalian cells originate from a tetraploid cell line.

In another embodiment, the concentration of PEG 3,000 is at or about 3% to at or about 4.5%.

In another embodiment, the concentration of PEG 6,000 is at or about 2.5% to at or about 3.5%.

In another embodiment, the concentration of Triton X100 is 0.05% (w/v).

In another embodiment, the mammalian cell culture broth is between 36° C. and 20° C.

In another embodiment, the mammalian cell culture broth is at or above 20° C.

In another embodiment, the flocculent from the primary settle is washed in a 9% sucrose solution.

DETAILED DESCRIPTION OF THE INVENTION

Figure 1:
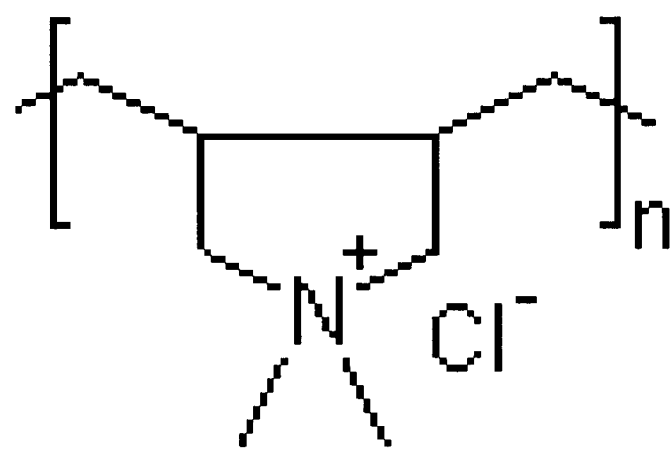
FIG. 1 provides the structure of PDADMAC.

The invention provides a simple harvest flocculation technique intended to maximize the recovery operation of high cell mass cell culture processes. Provided is a mammalian cell culture harvest method that makes use of cationic polymers in combination with non-ionic polymers in the flocculation of cell culture broth. Also provides is the use of cationic polymers in combination with both non-ionic polymers and non-ionic surfactants.

The invention is based on the discovery that using a non-ionic polymer or a non-ionic polymer and a non-ionic surfactant in combination with a cationic polymer to flocculate a mammalian cell culture broth decreased the flocculent settling time from 24 hours or longer to less than 1 hour, in some cases 15 minutes, independent of the cell culture process density (up to 44% packed cell volume) or lactate levels (10 g/L). The use of non-ionic polymers also resulted in removal of high order aggregates and host cell proteins that co-purify with the desired recombinant product. This simple harvest method maximized the recovery operation of cell culture processes, particularly high cell mass cell culture commercial level processes.

Flocculation is a process whereby particles in suspension form larger-size aggregates or clusters. In flocculation, particles come out of suspension in the form of floc by the addition of a flocculation agent or flocculent. Flocculents can be anionic or cationic polymers. There are natural flocculents such as alginates or Chitosan; mineral flocculents such as colloidal clays and activated silica; and synthetic flocculents such as polyacrylamides and poly diallyldimethyammonium chloride. Synthetic flocculents can be manufactured to have specific molecular weights (based on chain length) and molecular distribution.

Cationic polymers interact with negatively charged particles, such as organic substances. In cell culture broth, cationic polymers interact with negatively charged particles such as viable and non-viable cells, cell metabolites and the cellular debris such as nucleic acids, proteins and liposomes. Flocculation of negatively charged compounds found in cell culture broth with cationic polymers takes place through ionic interaction either via the bridging of the negatively charged particles; through patch binding of the cationic polymer that result in flocculation; or through charge neutralization of large negatively charged particles that result in the neutralized particle falling out of solution. Flocs formed by cationic polymer bridging of the negatively charged particles produced larger flocs and have increased shear sensitivity which result in floc disruption that produce higher levels of slower settling smaller particles. With patch or charge neutralization, cationic polymers with high charge densities interact with anionic patches on the particles in suspension, and either neutralized the charge on the particle or form larger particles that settled out of solution. Flocs formed in this manner have a smaller floc particle volume and are less prone to disruption due to shearing. For example, addition of poly diallyldimethyammonium chloride (PDADMAC) to cell culture broth flocculates negatively charged cells and cellular debris into larger particles via an electrostatic patch mechanism (Ramsden et al. (1998), Biotechnology Techniques, 12(8):599-603. PDADMAC also flocculates the negatively charged submicron particles to produce a feed stream with a significantly higher harvest filter train throughput compared to a typical centrifuged harvest feed stream. Flocculation via ionic interaction can be disrupted by increasing the salt concentration or altering pH.

The addition of a cationic polymer, such as poly diallyldimethyammonium chloride, to mammalian cell culture media that contains or has contained cells expressing recombinant proteins flocculates the negatively charged particles, including cells (viable and non-viable), cell metabolites and cellular debris. These large flocculated particles can be removed by centrifugation or by gravity settling. The setting rate or the time required for flocculated cells and cell debris to settle out is dependent on the density of cells, cell debris and cell metabolites. At low cell densities that are typical for batch cell culture process, the flocculated material typically settles out (no further settling) at some point over 4 hours to 24 hours, typically around 20-24 hours. Settling rates significantly decrease with cell culture processes that produce high cell densities of biomass (>10% packed cell volume), submicron cellular debris, and/or high lactate levels (>2-3 g/L). Cell culture processes that produced high cell densities or have elevated lactate levels require a significant amount of cell broth dilution for the floc to settle out in 24 hours. Despite the ease of using cationic polymers, such as PDADMAC as an alternative to traditional harvest methods, the prolonged settling times could be less desirable on a commercial scale.

The invention provides that flocculated particle size and the particle size growth rate in cationic polymer flocculated material are greatly enhanced in the presences of non-ionic polymers and non-ionic surfactants. Floc gravity settling times of less than 2 hours were routinely seen when PDADMAC was used in combination with non-ionic polymers such as polyethylene glycols and non-ionic surfactants, such as Triton X100, in spite of high biomass/cell densities that significantly increased the PDADMAC-only flocculation settling time. Shear forces that could disrupt the flocs and/or reduce flocculation rates were tolerated with the addition of non-ionic polymers and non-ionic surfactants. Harvest recovery yields of 80-90% or greater were consistently achieved with significantly reduced host DNA. Non-ionic polymer addition also reduces host cell proteins and some high molecular weight species.

As used herein, "cationic polymers" are positively charged polymers that bind to negatively charged suspended particles. Cationic polymers include, but are not limited to, polymers of diallyl dimethyl ammonium chloride (DADMAC). In a preferred embodiment, the polymerization of DADMAC forms an N-substituted pyrrolidine structure, PDADMAC (FIG. 1). Cationic polymers also include poly ethyleneimine (PEI), poly acrylamide (PAA) and chitosan.

Concentrations of at or about 20 pg to at or about 90 pg of PDADMAC per total cell density resulted in low supernatant turbidity and good floc settling. "Total cell density" is the sum of viable cells plus non-viable cells as measured by Trypan Blue exclusion using a Cedex Cell Counter and Analyzer. In one embodiment for small cell lines, such as a diploid cell line, PDADMAC is added at or about 25 pg/total cell density. In another embodiment, PDADMAC is added at or about 43 to at or about 57 pg/total cell density for larger cell lines, such as a tetraploid cell line.

PDADMAC at molecular weights from 200,000-500,000 impact flocculation performance by increasing sedimentation rate and supernatant clarity, compared to lower molecular weight forms. In one embodiment, the PDADMAC molecular weight is in the range of 400,000 to 500,000. In one embodiment, PDADMAC having a molecular weight in the range of 400,000-500,000 is used at a final concentration of 22 pg/Total cell density. In another embodiment, PDADMAC having a molecular weight in the range of 400,000-500,000 is used at a final concentration of 25 pg/Total cell density. In another embodiment, PDADMAC having a molecular weight in the range of 400,000-500,000 is used at a final concentration of 45 pg/Total cell density.

As used herein, "settling rate", "gravity settling rate" and "flocculated packed settling rate" are used interchangeably. Settling rates can be determined by methods known in the art and described herein. For example, gravity settling is at 1 g. Settling rates are determined by taking the floc volume divided by the total volume measured in a 0.5 L or 1 L glass graduated cylinder. Total volume is the volume of the cell broth with all flocculating/settling agents included.

"Settling time" is the time it takes the floc to have settled. Settling time is achieved when the floc settling rate is less than or equal to 1% per hour. Settling times of as little as 15 minutes for PDADMAC flocculation in combination with dosing of a non-ionic polymer or non-ionic polymers in combination with non-ionic surfactants are described herein. The rapid settling time occurred in spite of the high biomass/cell densities that significantly increase the PDADMAC-only flocculation settling time. Shear forces that disrupt the flocs and/or reduce flocculation rates are tolerated with the addition of non-ionic polymers or non-ionic surfactants.

Supernatant clarity is independent of the settling rate, but is dependent on the cationic polymer dosing level. Other factors such as temperature, cell culture fluid density and viscosity had little impact on settling rate or supernatant clarity. PDADMAC dosing, in particular, is a function of the cell volume, the total density of cells (viable and non-viable cells), and the concentration of submicron cellular debris particles.

As used herein, "non-ionic polymer" refers to hydrophilic polymers that increase interactions between molecules, enhancing precipitation. Non-ionic polymers include, but are not limited to, polyethylene glycols (PEG) maltodextran, starches, methyl celluloses, and dextrans.

Increased settling rates were achieved when PEG or dextrans were added to mammalian cell culture media simultaneously with or subsequent to the addition of a cationic polymer flocculent. Product recovery was dependent on the non-ionic polymer concentration, PEG molecular weight, order of addition of the non-ionic polymer and PDADMAC (simultaneously or PDADMAC first followed by the non-ionic polymer) and cell culture duration or debris level in the cell culture broth.

PEG 3,000 is useful in the range of at or about 3 to at or about 4.5% (w/v). PEG 6,000 is useful in the range of at or about 2.5% to at or about 3.5% (w/v). In one embodiment PEG 3,000 is used at a final concentration of 3% (w/v). In another embodiment, PEG 3,000 is used at a final concentration of 15% (w/v). In another embodiment, PEG 3,000 is used at a final concentration of 25% (w/v).

As used herein, "non-ionic surfactant" refers to organic compounds that are amphiphilic, meaning they contain both hydrophobic groups and hydrophilic groups and includes, but is not limited to, Sapoin and Triton X100 In one embodiment, Triton X-100 is used at a final concentration of 0.05% (w/v).

The non-ionic polymer can be added alone or in combination with a non-ionic surfactant. Either can be added simultaneously with the cationic polymer or subsequent to addition of cationic polymer. The non-ionic polymer and surfactant can both be added quickly with an addition time of 1 minute or less.

Once the flocculent has settled (primary settling), the clarified supernatant can be harvested. To increase recombinant product recovery, the floc can be washed or resuspended to remove any residual recombinant product. Suitable wash diluents include sucrose, PEG, cell culture media and buffer saline solution. In one embodiment, the wash diluent is 9% sucrose. The floc and wash diluent is mixed for <1 minute to 60 minutes and allowed to settle for ~1 hour to 24 hours. Once floc has settled (secondary settling) the clarified secondary supernatant is harvested. The supernatants from the primary and secondary settling can be combined or purified separately.

Clarified supernatant can be harvested by removing the supernatant by pumping or decanting followed by filtration through a depth filter containing diatomaceous earth and followed by a 0.2µ cut off membrane filter or just a 0.2µ cutoff filter.

Cationic polymer clearance can be monitored by methods known in the art, such as assays for monitoring mammalian cell toxicity; assays for determining the inhibition of DNA or RNA transcription by DNA polymerase or reverse transcription, and by assays that determine protein translation of mRNA; and by methods described herein. For example, PDADMAC clearance from the recombinant protein purification process intermediates can be monitored by inhibition of DNA amplification in using quantitative polymerase chain reaction (QPCR).

The cell culture broth can be used directly from the bioreactor or it can be cooled prior to flocculation. In a preferred embodiment the temperature range for the cell culture broth is from at or about 36° C. to at or about 20° C. In another embodiment, the cell culture broth is cooled to at or about 20° C.

The present invention provides a method of harvesting recombinant proteins from mammalian cell cultures. The typical methods used in commercial processes for the production of recombinant proteins by mammalian cell culture include batch culture, fed-batch and perfusion culture. Batch culture, a discontinuous method where cells are grown in a fixed volume of culture media for a short period of time followed by a full harvest. Harvest typically occurs at the point when the maximum cell density is achieved (typically $5-10 \times 10^6$ cells/mL. Fed-batch culture provides bolus or continuous media feeds to replenish those media components that have been consumed. Since fed-batch cultures receive additional nutrients throughout the run, they have the potential to achieve higher cell densities (>10 to $30 \times 10^6$ cells/ml) and increased product titers, when compared to the batch method. With perfusion methods, typical large scale commercial cell culture strategies strive to reach high cell densities, $60-90(+) \times 10^6$ cells/mL where almost a fifty to over one-half of the reactor volume is biomass. With perfusion culture, extreme cell densities of $>1 \times 10^8$ cells/mL have been achieved and even higher densities are predicted.

As used herein "peptide," "polypeptide" and "protein" are used interchangeably throughout and refer to a molecule comprising two or more amino acid residues joined to each other by peptide bonds. Peptides, polypeptides and proteins are also inclusive of modifications including, but not limited to, glycosylation, lipid attachment, sulfation, gamma-carboxylation of glutamic acid residues, hydroxylation and ADP-ribosylation. Polypeptides can be of scientific or commercial interest, including protein-based drugs. Polypeptides include, among other things, antibodies, fusion proteins, and cytokines. Peptides, polypeptides and proteins are produced by recombinant animal cell lines using cell culture methods and may be referred to as "recombinant peptide", "recombinant polypeptide" and "recombinant protein". The expressed protein(s) may be produced intracellularly or secreted into the culture medium from which it can be recovered and/or collected.

Examples of polypeptides that can be harvested using the methods of the invention include proteins comprising amino acid sequences identical to or substantially similar to all or part of one of the following proteins: tumor necrosis factor (TNF), flt3 ligand (WO 94/28391), erythropoietin, thrombopoeitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), *Gene* 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of proteins that can be produced according to the inventive methods may be found in, for example, *Human Cytokines: Handbook for Basic and Clinical Research, all volumes* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook, Vols.* 1 *and* 2 (Thompson and Lotze eds., Academic Press, San Diego, Calif., 2003).

Additionally the methods of the invention would be useful to harvest proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. No. 5,395,760 and U.S. Pat. No. 5,610,279), Interleukin-1 (IL-1) receptors (types I and II; EP Patent No. 0460846, U.S. Pat. No. 4,968, 607, and U.S. Pat. No. 5,767,064,), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be harvested using the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be harvested using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizomab, zalutumumab, and zanolimumab.

The invention can also be used to harvest recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262:1401-05; Harbury et al. (1994), *Nature* 371:80-83; Håkansson et al. (1999), *Structure* 7:255-64. Specifically included among such recombinant fusion proteins are proteins in which a portion of a receptor is fused to an Fc portion of an antibody such as etanercept (a p75 TNFR:Fc), and belatacept (CTLA4:Fc).

For the purposes of this invention, cell culture medium is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. The cell culture medium may or may not contain serum, peptone, and/or proteins. Various tissue culture media, including serum-free and defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

Cell culture media may be serum-free, protein-free, and/or peptone-free. "Serum-free" applies to a cell culture medium that does not contain animal sera, such as fetal bovine serum. "Protein-free" applies to cell culture media free from exogenously added protein, such as transferrin, protein growth factors IGF-1, or insulin. Protein-free media may or may not contain peptones. "Peptone-free" applies to cell culture media which contains no exogenous protein hydrolysates such as animal and/or plant protein hydrolysates. Cell culture broth or like terminology refers to the cell culture media that contains, among other things, viable and non-viable mammalian cells, cell metabolites and cellular debris such as nucleic acids, proteins and liposomes.

By cell culture or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, and operated in a batch, fed batch, continuous, semi-continuous, or perfusion mode are available for mammalian cell culture.

Mammalian cells, such as CHO cells, may be cultured in small scale cultures, such as for example, in 100 ml to large scale cell cultures, such as systems that have culture sizes in the thousand and tens of thousands mls, for clinical and commercial manufacturing of protein therapeutics.

The cell lines (also referred to as "host cells") are genetically engineered to express a polypeptide of commercial or scientific interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., *Large Scale Mammalian Cell Culture,* 1990, pp. 15-69.

A wide variety of mammalian cell lines suitable for growth in culture are available from the American Type Culture Collection (Manassas, Va.) and commercial vendors. Examples of mammalian cell lines commonly used in the industry include VERO, BHK, HeLa, CV1 (including Cos), MDCK, 293, 3T3, myeloma cell lines (e.g., NSO, NS1), PC12, WI38 cells, and Chinese hamster ovary (CHO) cells. CHO cells are widely used for the production of complex recombinant proteins, e.g. cytokines, clotting factors, and antibodies (Brasel et al. (1996), *Blood* 88:2004-2012; Kaufman et al. (1988), *J. Biol Chem* 263:6352-6362; McKinnon et al. (1991), *J Mol Endocrinol* 6:231-239; Wood et al. (1990), *J. Immunol.* 145:3011-3016). The dihydrofolate reductase (DHFR)-deficient mutant cell lines (Urlaub et al. (1980), *Proc Natl Acad Sci USA* 77: 4216-4220), DXB11 and DG-44, are desirable CHO host cell lines because the efficient DHFR selectable and amplifiable gene expression system allows high level recombinant protein expression in these cells (Kaufman R. J. (1990), *Meth Enzymol* 185:537-566). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of". The section headings used herein are for organizational purposes only and are not to be construed as limiting the subject matter described. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

This experiment compares different molecular weight preparations of diallyldimethylammonium chloride (PDADMAC) for flocculating mammalian cell culture broth and comparing their settling times.

CHO cells expressing a recombinant monoclonal antibody were grown in 2,000 L bioreactors in a fed batch culture for 15 days. Cell culture broth was cooled to 10° C. prior to testing. A series of spin flasks were set up with 1 L of cell culture broth in each flask. PDADMAC was supplied as 20% (w/v) liquid (Sigma Aldrich, St. Louis, Mo.) and a working stock solution used in all these experiments was prepared by diluting with purified water to 10% (w/v). PDADMAC, at molecular weights of 100,000-200,000; 200,000-350,000; and 400,000-500,000 was added to each flask to a final concentration between 29 and 86 pg PDADMAC per Total cell density. The PDADMAC solutions were added continuously for about 1 minute and incubated for 15 minutes, with stirring at 70-80 rpm at 10° C. The floc was allowed to settle at ambient temperature. This material was used for the settling time determination.

A second fed batch culture was grown in a 1,000 L disposable reactor for 15 days. The cell culture broth was maintained at ~36° C. A series of spin flasks were set up with 1 L of cell culture broth in each flask. PDADMAC at molecular weights of <100,000, 100,000-200,000; 200,000-350,000; and 400,000-500,000 was added to each flask to a final concentration between 25 and 76 pg PDADMAC per Total cell density. The PDADMAC solutions were added continuously for about 1 minute and incubated for 15 minutes, with stirring at 70-80 rpm at ~36° C. The floc was allowed to settle at ambient temperature. This material was used for the turbidity determination.

Total cell density was determined by adding the total number of viable cells to the total non-viable cells as measured by Trypan Blue exclusion using a Cedex Cell Counter and Analyzer (Roche Innovatis AG, Indianapolis, Ind.). The flocculated solutions were then transferred into 1 L glass graduated cylinders to determine flocculated packed settling rate. Readings were taken at 15 minute intervals for 90 minutes and the relative flocculation volume was calculated as Settled Floc Volume/Total Volume.

The supernatant was removed from the settled flocculated cell mass by decanting followed by 0.2μ filter. Turbidity was measured using a 2100P turbidimeter (Hach, Loveland, Colo.).

Figure 2A:
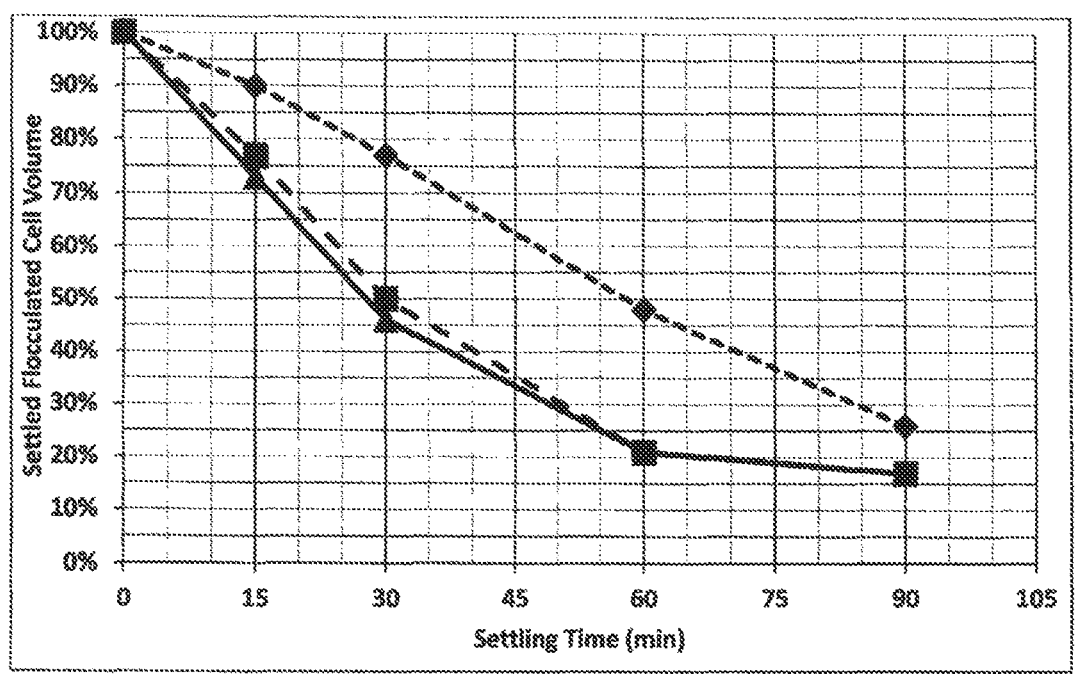
FIG. 2A shows the difference in settling times achieved by PDADMAC at various molecular weights. The concentration of PDADMAC at each molecular weight was 57 pg/Total cell density. The closed diamond/dashed line represents PDADMAC molecular weight 100,000-200,000. The closed square with dashed line represents PDADMAC molecular weight of 200,000-300,000. The closed triangle and solid line represents PDADMAC molecular weight of 400,000-500,000.
Figure 2B:
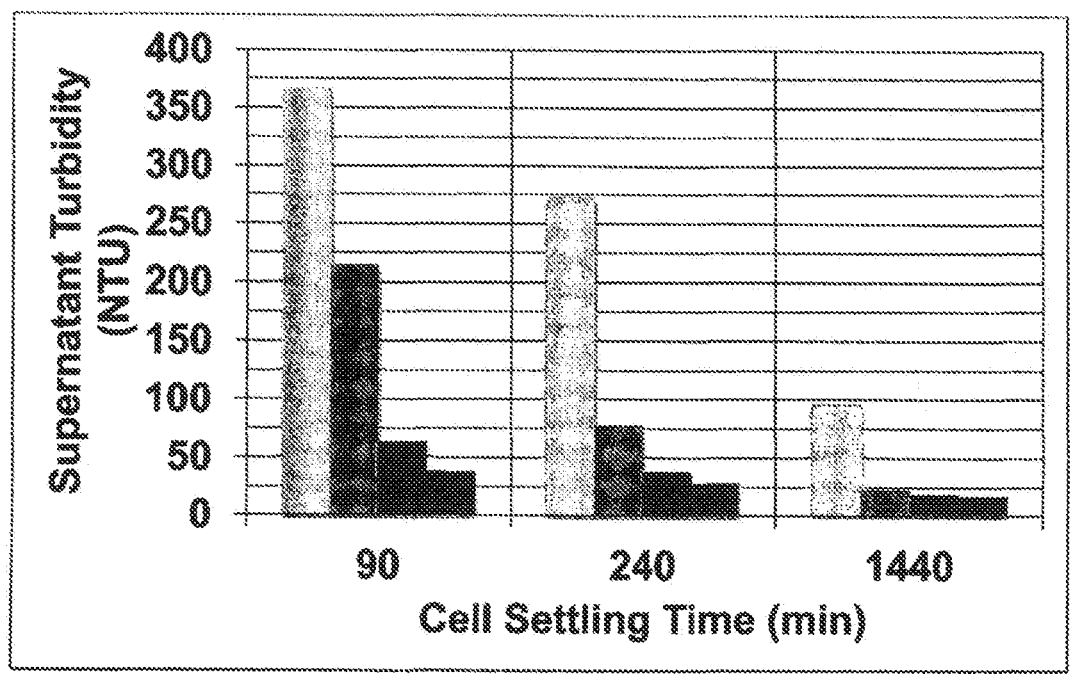
FIG. 2B shows the supernatant clarity achieved when flocculating cell culture broth with PDADMAC at various molecular weights. From left to right the bars represent PDADMAC molecular weight of <100,000; 100,000-200,000; 200,000-350,000; and 400,000-500,000.

FIGS. 2A and 2B show flocculation with PDADMAC having an average molecular weight greater than 200,000, but less than 500,000 results in an optimum settling time and clarity compared to PDADMAC with an average molecular weight less than 200,000.

Example 2

This experiment compares the amount of PDADMAC necessary for flocculating mammalian cell culture broth expressing a recombinant antibody from a small cell line, such as a diploid cell, and a large cell line, such as a tetraploid cell line.

Diploid and tetraploid cell lines were grown as described above. A series of spin flasks were set up with 1 L of cell culture broth in each flask from each of the diploid and tetraploid cultures. In this experiment and all the following experiments, unless otherwise noted, PDADMAC having an average molecular weight of 400,000 to 500,000 is used. PDADMAC was added to each flask to a final concentration as shown in Table 2. Total cell density was determined as described above.

TABLE 2

Final concentrations of PDADMAC for diploid and tetraploid cultures

| Cell Type | Final PDADMAC Concentration |
|---|---|
| 15-20 μm cells, such as a diploid cell | 11 pg per Total cell density |
| | 18 pg per Total cell density |
| | 25 pg per Total cell density |
| | 30 pg per Total cell density |
| 21-24 μm cells, such as a tetraploid cell | 29 pg per Total cell density |
| | 43 pg per Total cell density |
| | 57 pg per Total cell density |
| | 71 pg per Total cell density |
| | 86 pg per Total cell density |

The PDADMAC solutions were added continuously and stirred as described above. The floc was allowed to settle at ambient temperature.

Figure 3A:
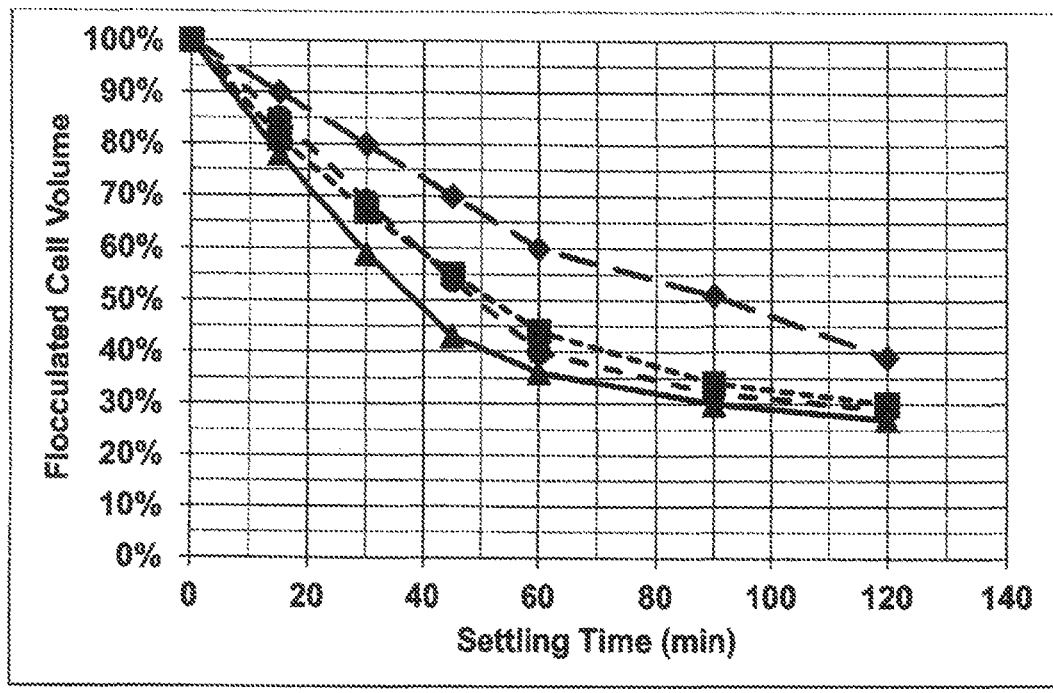
FIG. 3A shows the impact of high molecular weight PDADMAC concentration on flocculation of 15-20 μm cells. The closed diamond dashed line represents PDADMAC at 11 pg/Total cell density. The closed square with dashed line represents PDADMAC at 18 pg/Total cell density. The closed triangle with solid line represents PDADMAC at 25 pg/Total cell density. The closed circle with dashed line represents PDADMAC at 39 pg/Total cell density.

The flocculated solutions were then transferred into 1 L glass graduated cylinders to determine flocculated packed settling rate. Readings were taken at 15 minute intervals for 90 to 120 minutes and the relative flocculation volume was calculated as described above FIG. 3A shows flocculation with PDADMAC at a concentration of 25 pg per Total cell had the fastest settling time.

Figure 3B:
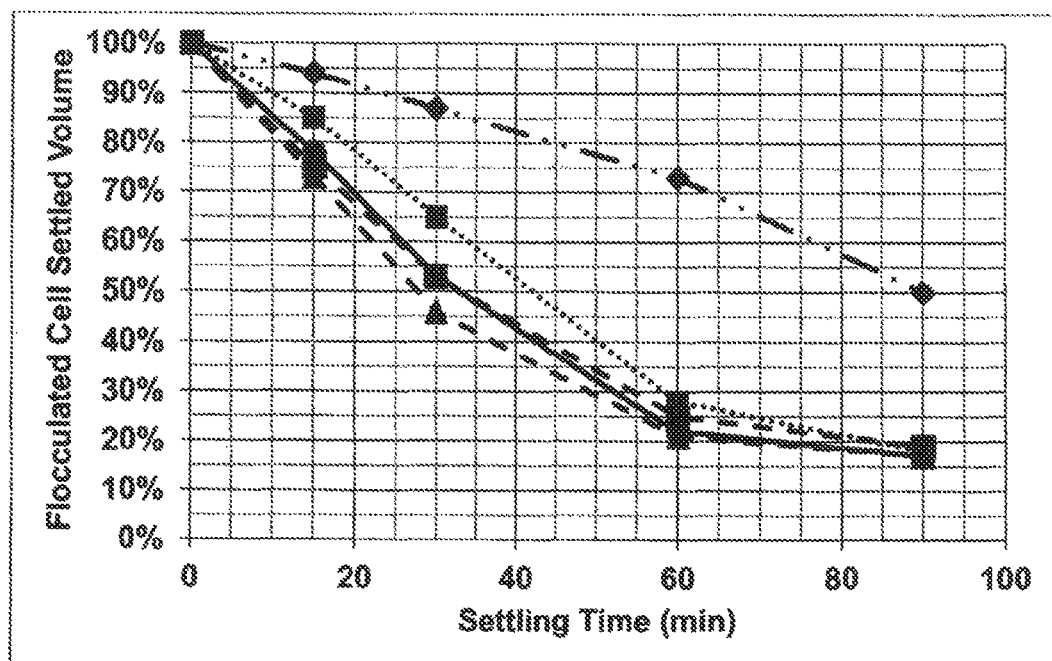
FIG. 3B shows the impact of high molecular weight PDADMAC concentration on flocculation of 21-24 μm cells. The closed diamond dot and dashed line represents PDADMAC at 29 pg/Total cell density. The closed square with dashed line represents PDADMAC at 43 pg/Total cell density. The closed triangle with dashed line represents PDADMAC at 57 pg/Total cell density. The closed circle with solid line represents PDADMAC at 71 pg/Total cell density. The closed square with dotted line represents PDADMAC at 86 pg/Total cell density.

FIG. 3B shows flocculation with PDADMAC at a concentration of 57 pg per Total cell had the fastest settling time.

Example 3

This experiment looks at the impact of PDADMAC flocculation for cell cultures that produce high lactate levels and/or have high cell densities.

CHO cells expressing a recombinant monoclonal antibody were grown in 1,000 L disposable bioreactor for 14 days. The cell culture broth was at ambient temperature. Four spin flasks were set up with 1 L of cell culture broth in each flask. Prior to adding the PDADMAC, each flask was spiked with either 3 g/L, 6 g/L or 9 g/L Na DL-Lactate, at 60% (w/w) (Sigma Aldrich, St. Louis, Mo.), or a no lactate as a control. PDADMAC was then added to each flask to a final concentration of 25 pg/Total cell density (PDADMAC stock as described above). Total cell density was determined as described above.

PDADMAC was added continuously at ambient temperature and stirred as described above. The floc was then allowed to settle at ambient temperature.

The flocculated solutions were then transferred into 1 L glass graduated cylinders to determine flocculated packed settling rate. Readings were taken at various intervals for 1500 minutes and the relative flocculation volume was calculated as described above.

A second batch of CHO cell cultures were grown in a 1,000 L disposable bioreactor, in a perfusion culture for 20 days. Cell broth was cooled to ambient temperature. Prior to PDADMAC addition, the cell broth was diluted 25%, 50% and 75% with cell culture medium. Cell broth at a packed cell volume of 44% was not diluted prior to PDADMAC addition. The final concentration of PDADMAC was 25 to 26 pg/Total cell density. The PDADMAC addition rate was ~1 minute, with stirring and settling at ambient temperature as described above.

The flocculated solutions were then transferred into 1 L glass graduated cylinders to determine flocculated packed settling rate. Readings were taken at various intervals for 1400 minutes and the relative flocculation volume was calculated as described above.

Figure 4A:
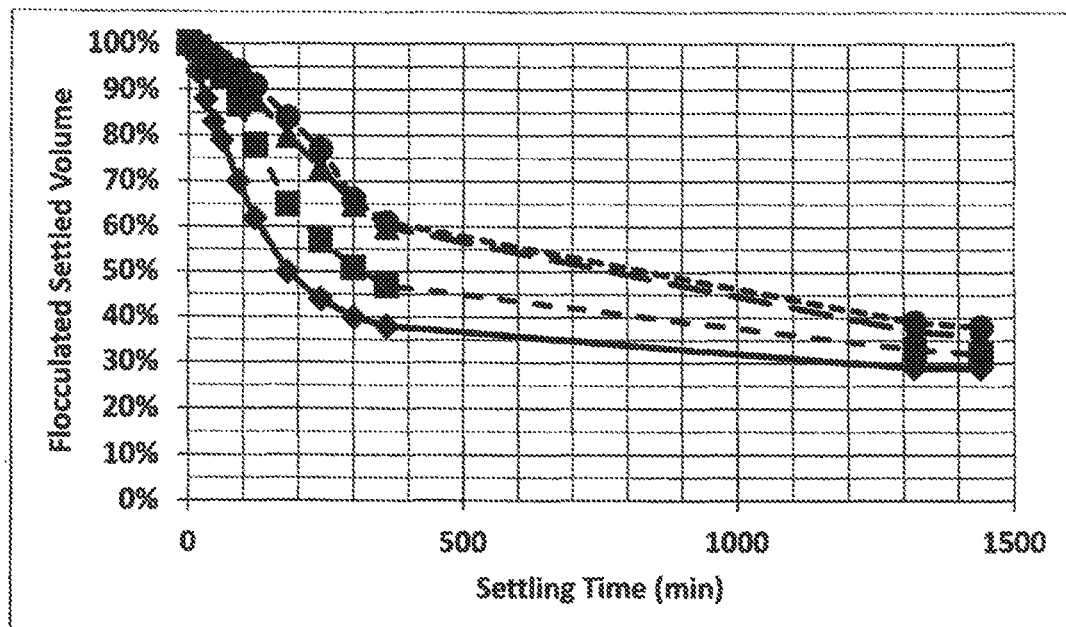
FIG. 4A shows the impact of high molecular weight PDADMAC flocculation for cell cultures that product high lactate levels. The solid diamond with solid line represents no added lactate. The solid square with dashed line represents lactate spiked at 3 g/L. The solid triangle with dashed line represents lactate spiked at 6 g/L. The solid circle with dashed line represents lactate spiked at 9 g/L.
Figure 4B:
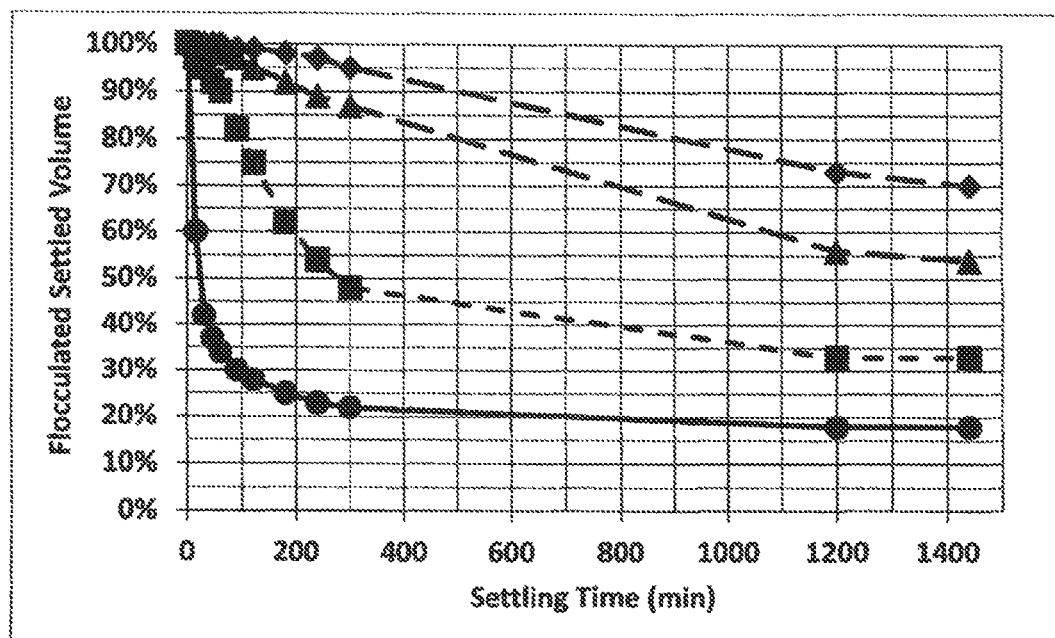
FIG. 4B shows the impact of high molecular weight PDADMAC flocculation for cell cultures that have high cell density as measured by packed cell volume (PCV). The solid diamond with dashed line represents 44% PCV. The solid triangle with dashed line represents 33% PCV. The solid square with dashed line represents 22% PCV. The solid circle with solid line represents 11% PCV.

FIGS. 4A and 4B show that settling rates significantly decrease with cell culture processes that have high lactate levels (>2-3 g/L) and/or produce high cell densities of biomass (>10% packed cell volume).

Example 4

This experiment compares the settling times of different diluents used in combination with PDADMAC.

CHO cells expressing a recombinant monoclonal antibody were grown in a 1,000 L disposable bioreactor in a perfusion culture for 18 days. Cell broth from Day 16 was delivered for testing at 36° C. and was cooled down to ambient temperature for 2.5 hours prior to flocculation. Addition and settling was performed at ambient. Prior to PDADMAC addition, the cell broth was diluted to 67% with the various diluents. Lactate level was 5 g/L. PDADMAC addition rate ~1 minute with an incubation period of 15 minutes at 75-85 rpm. PDADMAC stock solution was at 10% (w/v) from the original stock solution of 20 (w/v) with purified water. Final concentration of PDADMAC was 25 pg/Total cell density. The floc was allowed to settle at ambient temperature.

A series of diluents was prepared; the concentrations are shown in Table 3.

TABLE 3

Final concentrations of various diluents

| Compound | Final Concentration |
| --- | --- |
| Sucrose (EMD, Philadelphia, PA) | 90 g/L |
| Betaine (Sigma Aldrich, St. Louis, MO) | 32 g/L |
| PEG 1,000 (Sigma Aldrich, St. Louis, MO) | 146 g/L |
| PEG 6,000 (Sigma Aldrich, St. Louis, MO) | 260 g/L |
| Dextran 70/Betaine (Sigma Aldrich, St. Louis, MO) | Dextran 100 g/L Betaine 30 g/L |
| Cell culture medium | Control |

The flocculated solutions were then transferred into 1 L glass graduated cylinders to determine flocculated packed settling rate. Readings were taken at various intervals for 1600 minutes and the relative flocculation volume was calculated as described above.

Figure 5:
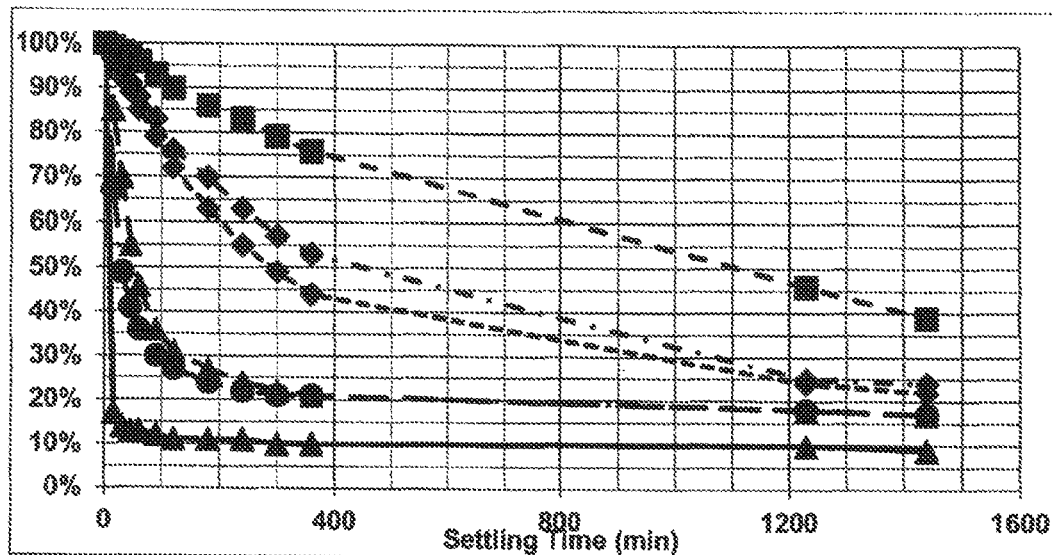
FIG. 5 shows the impact of various diluents on high molecular weight PDADMAC flocculation for a cell culture process with high lactate levels. The solid triangle with the dotted and dashed line represents Sucrose. The solid square with dashed line represents cell culture media with no diluents. The solid diamond with dashed line represents Betaine. The solid circle with dashed line represents PEG 1,000. The solid triangle with the solid line represents PEG 6,000. The solid triangle with the dashed line represents Dextran 70 and Betaine.

As shown in FIG. 5, the combination of PDADMAC and PEG 6,000 has the fastest settling time. The combination of PDADMAC with PEG 6,000, PEG 1,000 or Dextran 70/Betaine had improved settling rates compared to PDADMAC alone. The addition of non-ionic polymers significantly increased the floc settling rate. The combination of PDADMAC with either PEG or Dextran also decreased settling time compared to PDADMAC alone, independent of lactate levels in the culture.

Example 5

This experiment looks at the impact of the combination of PDADMAC and PEG 3,000 on settling times for cell cultures with high cell densities.

CHO cells expressing a recombinant monoclonal antibody were grown in 80 L bioreactor in a perfusion culture for 20 days. Cell culture broth was cooled to ambient temperature prior to testing. Prior to PDADMAC addition, the cell broth was diluted to 10% with the 36% (w/v) Sucrose or 25% (w/v) PEG 3,000 (both in purified water). Final cell broth sucrose concentration was 3.6% (w/v) and the final PEG 3,000 concentration was 2.5% (w/v). PDADMAC addition rate ~1 minute with a incubation period of 15 minutes at 75-85 rpm. PDADMAC stock solution was at 10% (w/v) from the original stock solution of 20 (w/v) with purified water. Final concentration of PDADMAC was 22 pg/Total cell density for PEG 3,000 and 25 pg/Total cell density for Sucrose and control or undiluted cell broth. Control or undiluted cell broth PCV was 48%. The diluted cell broth PCV=(control PCV× dilution factor)=43.2%.

The flocculated solutions were then transferred into 1 L glass graduated cylinders to determine flocculated packed settling rate. Readings were taken at various intervals for 240 minutes and the relative flocculation volume was calculated as described above.

Figure 6:
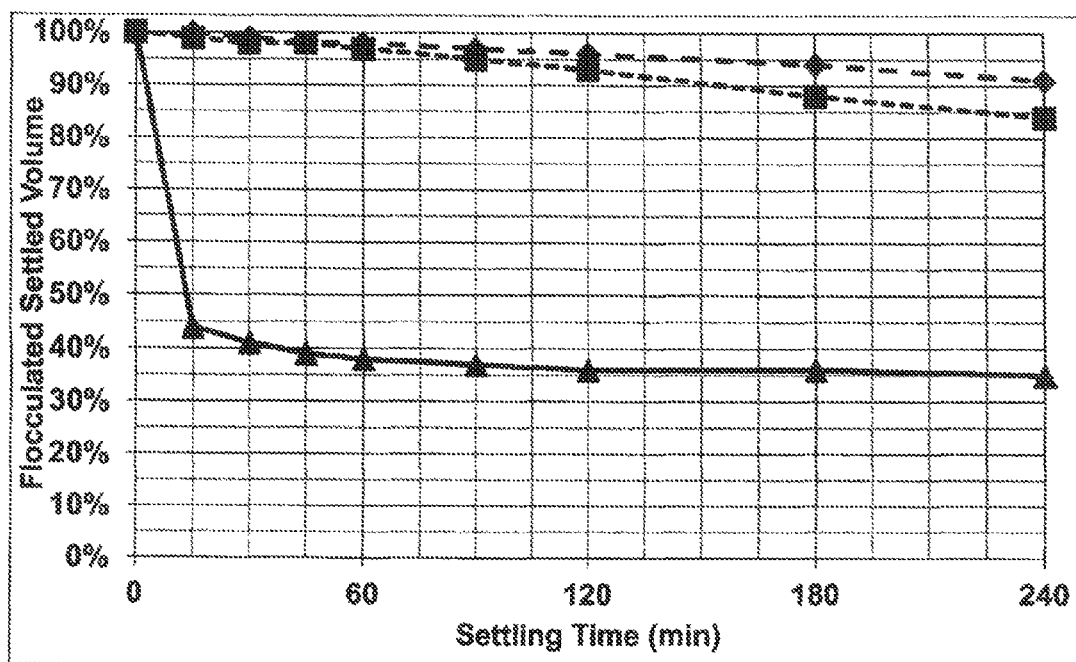
FIG. 6 shows the impact of PDADMAC/PEG flocculation for cell cultures with a PCV of 43.2%. The solid diamond with dashed line represents PDADMAC only. The solid square with dashed line represents Sucrose. The solid triangle with solid line represents PDADMAC/PEG.

As shown in FIG. 6, the combination of PDADMAC and PEG 3,000 resulted in more rapid settling than PDADMAC alone. As seen in Example 3, the settling rate for PDADMAC alone significantly decreased with an increase in cell density. The combination of PEG 3,000 with PDADMAC decreased the flocculent settling time over that of PDADMAC alone, independent of the cell culture process density (in this case 43% packed cell volume).

Example 6

This experiment looks at the impact of the timing of the PEG addition with PDADMAC on settling times.

CHO cells expressing a recombinant monoclonal antibody were grown in 80 L bioreactor in a 19 day perfusion cell culture process. Cell culture broth was cooled to 21° C. Three spin flasks were set up with 1 L of cell culture broth in each flask. To one flask PDADMAC was added at a concentration of 45 pg/Total cell density (molecular weight 400,000-500,000). To another flask PDADMAC 45 pg/Total cell density and PEG 3,000, 15% (w/v) were added as a bolus addition (the 1-Step Method). To the third flask, PDADMAC was added at a concentration of 45 pg/Total cell density and PEG 3,000 at a final concentration of 15% (w/v) was added following the PDADMAC addition (the 2-Step Method). PDADMAC addition rate was ~1 minute. PDADMAC/PEG addition rate was ~5 minutes. All additions were at ambient temperature. All flasks were incubated for 15 minutes at 75-85 rpm. The floc was allowed to settle at ambient temperature.

The flocculated solutions were then transferred into 1 L glass graduated cylinders to determine flocculated packed settling rate. Readings were taken at various intervals for 240 minutes and the relative flocculation volume was calculated as described above.

Figure 7:
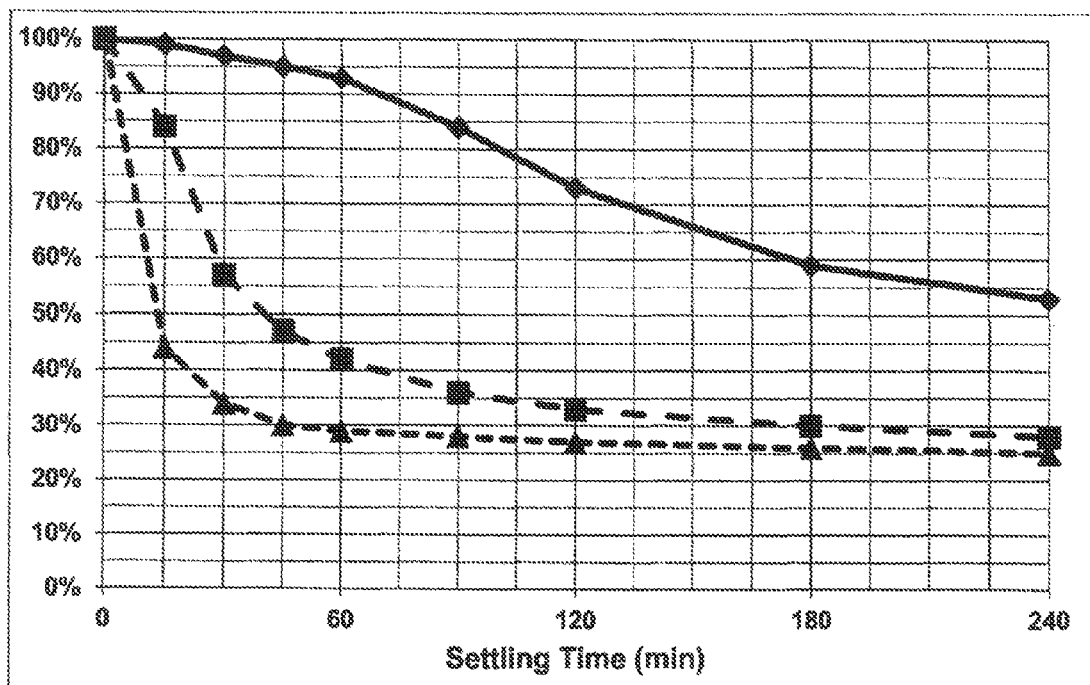
FIG. 7 shows the impact of the order of addition of PDADMAC and PEG. PDADMAC and PEG bolus addition (1 step method) is shown by the solid triangle with the dashed line. PDADMAC addition followed by PEG addition (2 stem method) is shown by the solid square with dashed line. PDADMAC alone is shown by the solid diamond with the solid line.

As shown in FIG. 7, the combination of PDADMAC and PEG 3,000 either added simultaneously or sequentially decreased the flocculent settling time over that of PDADMAC alone.

A large scale culture was next prepared. CHO cells expressing a recombinant monoclonal antibody were grown in an 80 L bioreactor in a perfusion culture for 19 days. Cell culture broth was cooled to 21° C. PDADMAC at a concentration of 45 pg/Total cell density and PEG 3,000 at a final concentration of 15% (w/v) were added simultaneously at ambient temperature, addition rate was 21 minutes, followed by 5 minute incubation at 100 rpm. The floc was allowed to settle at ambient temperature.

Once the flocculent has settled (primary settling), the clarified supernatant was be harvested by pumping the fluid from the bioreactor followed by filtration through a depth filter containing diatomaceous earth followed by a 0.2µ cut off membrane filter.

The floc was washed in an equal volume of 9% sucrose solution to remove any residual recombinant protein and allowed to settle for 16 hours. Once floc settled (secondary settling) the clarified secondary supernatant was harvested as described above.

Clarified harvested cell culture supernatants from the above flocculations (small scale and large scale) were purified using Protein A chromatography followed by a product quality determination. The Protein A eluate was not neutralized prior to product quality determination. Protein A eluate product quality attributes measured were molecular variants as measured by SEC, host cell proteins as determined by ELISA.

The Protein A purified material was then passed over a CEX column at pH 7.5.

compared to the primary PDADMAC/PEG harvest and is believed to be the resolubization of these impurities.

Example 7

This experiment looks at the impact on settling time by adding a surfactant along with PDADMAC and PEG.

CHO cells expressing a recombinant monoclonal antibody were grown in an 80 L bioreactor in a perfusion cell culture for 15 days. Cell broth from day 14 was cooled to 30° C. for testing. Two spin flasks were set up with 1 L of cell culture broth in each flask. To one flask PDADMAC and PEG 3,000 were added simultaneously, PDADMAC was added at a concentration of 25 pg/Total cell density (molecular weight 400, 000-500,000) and PEG 3,000 at a final concentration of 3% (w/v). To the other flask Triton X-100 at a final concentration of 0.05% (v/v) was added in addition to PDADMAC and PEG at the above concentrations. (Triton X-100 stock solution was at 10% (v/v) from an original stock solution of 20% (v/v), Sigma Aldrich, St. Louis, Mo.) The three components were added simultaneously. The addition rate was ~1 minute, with incubation for 15 minutes at 75-85 prm. All flasks were spun as described in earlier examples. The floc was allowed to settle at ambient temperature.

The flocculated solutions were then transferred into 1 L glass graduated cylinders to determine flocculated packed settling rate. Readings were taken at various intervals for 240 minutes and the relative flocculation volume was calculated as described above.

Figure 8:
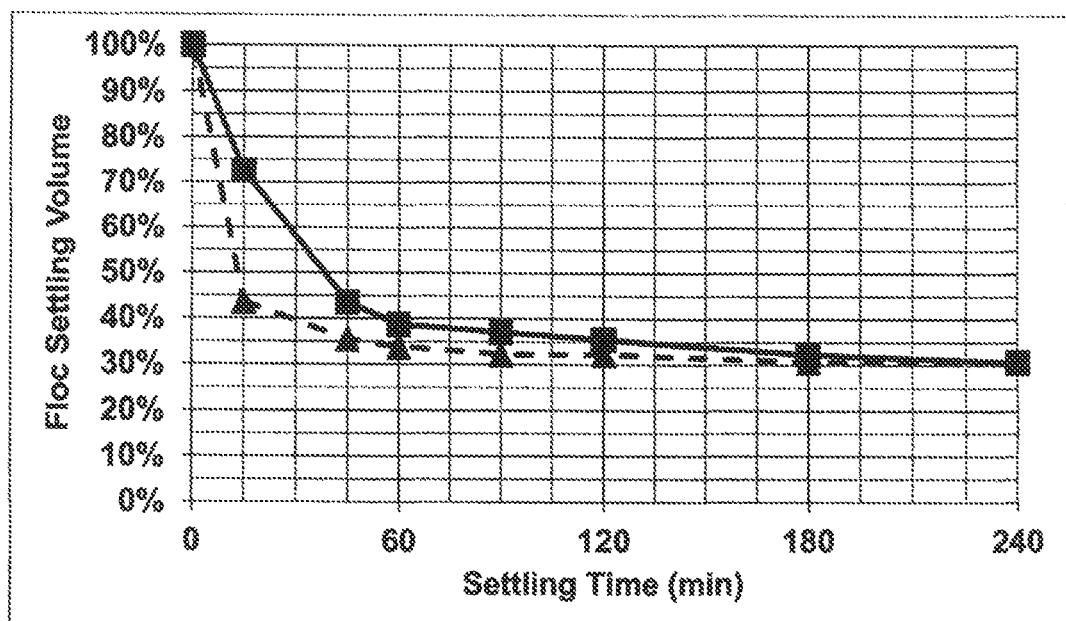
FIG. 8 shows the impact of addition of Triton X-100. PDADMAC/PEG addition is shown by the solid square with the solid line. PDADMAC/PEG/Triton X-100 addition is shown by the solid triangle with the dashed line.

As shown in FIG. 8, the addition of Triton X-100 along with PDADMAC and PEG 3,000, decreased the flocculent settling time over that of PDADMAC and PEG 3,000 alone.

What is claimed is:

1. A mammalian cell culture harvest method comprising culturing mammalian cells expressing a recombinant protein in a cell culture medium for a predetermined time or until a desired cell density and/or packed cell volume is achieved,
adding a cationic polymer selected from the group consisting of: a polymer of diallyldimethyammonium chloride and a polymer of polydiallyldimethyammonium chlo-

TABLE 4

| | | | | | | | CEX @ pH 7.5 | |
| | | SEC | | CHOP | | | Post- | |
| Harvest | HMW | Monomer | LMW | (ppm) | Pre | Main | Shoulder | Post |
| Control | 11.6% | 87.2% | 1.2% | 9,602 | 8.7% | 82.9% | 6.8% | 1.6% |
| Small Scale 2 Step Method | 9.2% | 89.6% | 1.2% | 3,950 | 8.2% | 83.5% | 6.8% | 1.6% |
| Small Scale 1 Step Method | 9.0% | 89.8% | 1.2% | 3,602 | 8.2% | 83.5% | 6.8% | 1.5% |
| Large Scale Primary Settle | 9.6% | 89.2% | 1.2% | 5,056 | 8.1% | 83.5% | 7.0% | 1.4% |
| Large Scale Secondary Settle with Sucrose Wash | 11.7% | 86.9% | 1.5% | 11,268 | 8.4% | 83.8% | 6.4% | 1.5% |

Product quality is similar between the control and the primary flocculate harvest for both scales. The PDADMAC/PEG primary harvest tends to remove the higher order aggregate which is reflected by the low HMW levels in the Protein A pool. A reduction in the host cell protein level for PDADMAC/PEG harvest was observed. The resuspension with sucrose resulted in slightly higher levels of CHOP and HMW ride, and a non-ionic polymer selected from the group consisting of: polyethyleneglycol and dextran to the cell culture medium initiating flocculation, mixing the cell culture medium during flocculation, allowing the flocculent to settle for a primary settle, and recovering the primary clarified supernatant.

2. The mammalian cell culture harvest method according to claim 1, wherein the non-ionic polymer is selected from PEG 3,000 and PEG 6,000.

3. The mammalian cell culture harvest method according to claim 1, further comprising adding a non-ionic surfactant to the cell culture medium.

4. The mammalian cell culture harvest method according to claim 3, wherein the non-ionic surfactant is Triton X-100.

5. The mammalian cell culture harvest method according to claim 1, further comprising
washing the primary settle flocculent,
allowing the washed flocculent to settle for a secondary settle, and
recovering the secondary clarified supernatant.

6. The method according to claim 1, where the cationic polymer and the non-ionic polymer are added simultaneously.

7. The method according to claim 1, where the cationic polymer is added first and mixed for at least 30 seconds followed by addition of the non-ionic polymer.

8. The method according to claim 1, where the cationic polymer, the non-ionic polymer and a non-ionic surfactant are added simultaneously.

9. The method according to claim 1, where the cationic polymer is added first and mixed for at least 30 seconds followed by addition of the non-ionic polymer and a non-ionic surfactant.

10. The method according to claim 3, wherein the non-ionic surfactant is Sapoin or Triton X100.

11. The method according to claim 1, wherein the poly diallyldimethyammonium chloride is added at a concentration of at or about 20 to at or about 90 pg/total cell density.

12. The method according to claim 1, wherein the poly diallyldimethyammonium chloride is added at a concentration of at or about 25 pg/total cell density wherein the mammalian cells originate from a diploid cell line.

13. The method according to claim 1, wherein the poly diallyldimethyammonium chloride is added between 43 pg/total cell density and 57 pg/total cell density wherein the mammalian cells originate from a tetraploid cell line.

14. The method according to claim 2, wherein the concentration of PEG 3,000 is at or about 3% to at or about 4.5%.

15. The method according to claim 2, wherein the concentration of PEG 6,000 is at or about 2.5% to at or about 3.5%.

16. The method according to claim 4, wherein the concentration of Triton X100 is 0.05% (w/v).

17. The method according to claim 1, wherein the mammalian cell culture medium is between 36° C. and 20° C.

18. The method according to claim 1, wherein the mammalian cell culture medium is at or above 20° C.

19. The method according to claim 5, wherein the flocculent from the primary settle is washed in a 9% sucrose solution.

* * * * *